US006978178B2

(12) United States Patent
Sommer et al.

(10) Patent No.: US 6,978,178 B2
(45) Date of Patent: Dec. 20, 2005

(54) METHOD AND APPARATUS FOR SELECTING AN OPTIMAL ELECTRODE CONFIGURATION OF A MEDICAL ELECTRICAL LEAD HAVING A MULTIPLE ELECTRODE ARRAY

(75) Inventors: John L. Sommer, Coon Rapids, MN (US); Yong Kyun Cho, Maple Grove, MN (US); Lawrence C. McClure, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 331 days.

(21) Appl. No.: 10/137,248

(22) Filed: Apr. 30, 2002

(65) Prior Publication Data

US 2003/0204232 A1 Oct. 30, 2003

(51) Int. Cl.[7] .................. A61N 1/365; A61N 1/368
(52) U.S. Cl. ........................... 607/28; 607/27
(58) Field of Search .................. 607/8–9, 27–28, 607/120–123, 126

(56) References Cited

U.S. PATENT DOCUMENTS

| 3,757,792 | A | 9/1973 | Mulier et al. ............ 128/419 P |
|---|---|---|---|
| 4,106,512 | A | 8/1978 | Bisping ....................... 128/418 |
| 4,217,913 | A | 8/1980 | Dutcher ....................... 128/785 |
| 4,390,023 | A | 6/1983 | Rise ............................ 607/66 |
| 4,660,571 | A | 4/1987 | Hess et al. .................. 128/784 |
| 4,662,382 | A | 5/1987 | Sluetz et al. ................ 128/785 |
| 4,711,251 | A | 12/1987 | Stokes ........................ 128/784 |
| 4,922,607 | A | 5/1990 | Doan et al. .................... 29/879 |
| 4,946,457 | A | 8/1990 | Elliott ........................... 606/1 |
| 5,117,824 | A | 6/1992 | Keimel et al. .......... 128/419 D |
| 5,246,014 | A | 9/1993 | Williams et al. ............ 607/122 |
| 5,324,310 | A | 6/1994 | Greeninger et al. .......... 607/28 |
| 5,462,545 | A | 10/1995 | Wang et al. .................. 606/41 |
| 5,534,018 | A | 7/1996 | Wahlstrand et al. .......... 607/27 |
| 5,584,873 | A | 12/1996 | Shoberg et al. ............ 607/122 |
| 5,601,615 | A | * 2/1997 | Markowitz et al. ........... 607/28 |
| 5,643,330 | A | 7/1997 | Holsheimer et al. .......... 607/46 |
| 5,662,699 | A | 9/1997 | Hamedi et al. ............. 607/138 |
| 5,683,431 | A | 11/1997 | Wang .......................... 607/28 |
| 5,741,214 | A | 4/1998 | Ouchi et al. ................. 600/374 |
| 5,755,664 | A | 5/1998 | Rubenstein ................. 600/377 |
| 5,775,331 | A | 7/1998 | Raymond et al. ........... 600/554 |
| 5,800,465 | A | * 9/1998 | Thompson et al. ............ 607/9 |
| 5,824,030 | A | 10/1998 | Yang et al. ................. 607/122 |
| 5,836,875 | A | 11/1998 | Webster, Jr. ................ 600/374 |
| 5,861,012 | A | 1/1999 | Stroebel ....................... 607/28 |
| 5,916,158 | A | 6/1999 | Webster, Jr. ................ 600/374 |
| 5,987,746 | A | 11/1999 | Williams ..................... 29/876 |
| 6,064,905 | A | 5/2000 | Webster, Jr. et al. ........ 600/424 |

(Continued)

FOREIGN PATENT DOCUMENTS

WO    WO 01/74441    10/2001    ............ A61N 1/00

Primary Examiner—Carl Layno
(74) Attorney, Agent, or Firm—Michael C. Soldner; Girma Wolde-Michael

(57) ABSTRACT

An electrical medical lead is provided having two or more electrodes, electrically insulated from each other and electrically coupled to individually insulated filars in a multi-filar coiled conductor. When the lead is used with a medical device equipped with a switch matrix, electrodes are selected individually or simultaneously to serve as an anode or cathode in any unipolar, bipolar or multi-polar configuration for delivering stimulation and/or sensing signals in excitable tissue. In one embodiment, a tip electrode array is expandable for improving electrode contact with targeted tissue and stabilizing lead position.

12 Claims, 10 Drawing Sheets

U.S. PATENT DOCUMENTS

| | | |
|---|---|---|
| 6,071,279 A | 6/2000 | Whayne et al. ............... 606/41 |
| 6,078,830 A | 6/2000 | Levin et al. ................ 600/374 |
| 6,085,118 A | 7/2000 | Hirschberg et al. ........... 607/9 |
| 6,161,029 A | 12/2000 | Spreigl et al. .............. 600/381 |
| 6,205,360 B1 | 3/2001 | Carter et al. .................. 607/57 |
| 6,317,633 B1 | 11/2001 | Jorgenson et al. ............ 607/28 |
| 6,643,546 B2 * | 11/2003 | Mathis et al. .................. 607/9 |
| 2003/0083724 A1 * | 5/2003 | Jog et al. .................... 607/122 |

* cited by examiner

METHOD AND APPARATUS FOR SELECTING AN OPTIMAL ELECTRODE CONFIGURATION OF A MEDICAL ELECTRICAL LEAD HAVING A MULTIPLE ELECTRODE ARRAY

FIELD OF THE INVENTION

The present invention relates generally to an implantable electrical stimulation and/or sensing lead, and more particularly, the present invention relates to a method and apparatus for improved stimulation and sensing of a medical electrical lead having a multiple electrode array.

BACKGROUND OF THE INVENTION

A wide assortment of implantable medical devices (IMDs) are presently known and in commercial use. Such devices include cardiac pacemakers, cardiac defibrillators, cardioverters, neurostimulators, and other devices for delivering electrical signals to excitable tissue and/or receiving signals from the tissue. Devices such as pacemakers, whether implantable or temporary external type devices, are part of a system for delivering an electrical therapy or monitoring a patient condition. In addition to the pacemaker device, which typically has some form of pulse generator, a pacing system includes one or more leads carrying electrodes for delivering generated stimulation pulses to the heart and for sensing cardiac signals.

Pacemakers treat heart conditions in which the heart beats at a rate that is considered to be too slow, commonly referred to as bradycardia, by sensing cardiac signals and delivering appropriately timed electrical stimulation pulses to the atria and/or ventricles as needed to cause the myocardium to contract. Pacemakers may sense intrinsic cardiac signals that occur when the myocardium depolarizes naturally, causing a normal myocardial contraction or heart beat. A sensed signal associated with ventricular contraction is referred to as an R-wave, and a sensed signal associated with atrial contraction is a P-wave. When an intrinsic R-wave or P-wave is not sensed by the pacemaker, a stimulation pacing pulse is delivered, eliciting an evoked response which causes the myocardium to contract, thus maintaining a desired heart rate.

Pacemakers operate in either a unipolar or bipolar mode, and pace the atria and/or the ventricles of the heart. Unipolar pacing requires a lead having only one distal electrode for positioning in the heart, and utilizes the case, or housing of the implanted device as the other electrode for the pacing and sensing operations. For bipolar pacing and sensing, the lead typically has two electrodes, a tip electrode disposed at the distal end of the lead, and a ring electrode spaced somewhat back from the distal end. Each electrode is electrically coupled to a conductive cable or coil, which carries the stimulating current or sensed cardiac signals between the electrodes and the implanted device via a connector.

Combination devices are available for treating both fast and slow cardiac arrhythmias by delivering electrical shock therapy for cardioverting or defibrillating the heart in addition to cardiac pacing therapies. Such a device, commonly known as an implantable cardioverter defibrillator or "ICD", uses coil electrodes for delivering high-voltage shock therapies. An implantable cardiac lead used in combination with an ICD may be a tripolar or quadrapolar lead equipped with a tip electrode and a ring electrode for pacing and sensing functions and one or two coil electrodes for shock therapies.

In order to achieve stimulation or sensing in the right side of the heart, a lead may be positioned against the endocardium by advancing the lead through the vena cava into the right atrium for right atrial applications, or further advancing the lead into the right ventricle for right ventricular applications. In order to achieve stimulation or sensing in the left heart chambers, a lead, often referred to as a "coronary sinus lead," may be positioned within the vasculature of the left side of the heart via the coronary sinus and great cardiac vein. This endovascular lead placement is sometimes referred to as "epicardial" placement since electrodes on a coronary sinus lead will sense or stimulate epicardial heart tissue.

In order to work reliably, cardiac leads need to be positioned and secured at a targeted cardiac tissue site in a stable manner. Unacceptable pacing or sensing thresholds measured during an implant procedure may require lead repositioning. Shifting or dislodgement of the lead over time may result in changing thresholds, sometimes requiring programming adjustments in order to maintain an appropriate level of therapy. At the same time, increased pacing thresholds decrease the useful life of the battery in the implantable device, requiring earlier device replacement. Poor or inaccurate sensing of naturally occurring heart signals may result in inappropriate withholding or delivery of therapy.

To address these problems, an electrode may be passively secured in a desired endocardial position by the use of tines located at the distal end of a lead. The tines engage with the endocardial trabeculae, holding the distal lead end in place. Alternatively, an electrode may be actively secured by the use of a rotatable fixation helix. The helix exits the distal end of the lead and can be screwed into the body tissue. The helix itself may serve as an electrode or it may serve exclusively as an anchoring mechanism to locate an electrode mounted on the lead adjacent to a targeted tissue site. The fixation helix may be coupled to a drive shaft that is further connected to a coiled conductor that extends through the lead body as generally described in U.S. Pat. No. 4,106,512 issued to Bisping et al. A physician rotates the coiled conductor at a proximal end to cause rotation of the fixation helix via the drive shaft. As the helix is rotated in one direction, the helix is secured in the cardiac tissue. Rotation of the fixation helix in the opposite direction removes the helix from the tissue to allow for repositioning of the lead at another location.

These fixation methods, however, are not entirely appropriate in left heart stimulation and sensing applications when the lead is positioned endovascularly. A helical coil would puncture a cardiac vein. Tines would make lead re-positioning difficult because retraction of a tined lead within a narrow vein could potentially damage the valves within the vein. Tissue encapsulation of various passive and active fixation devices is normally encouraged to further stabilize an endocardial lead position. Tissue encapsulation is undesirable in stabilizing an endovascular lead, however, since such tissue ingrowth may obstruct blood flow. Methods for stabilizing an endovascular lead must allow for unimpeded blood flow. One method for stabilizing an endovascular lead is disclosed in U.S. Pat. No. 6,161,029, issued to Spreigl, et al., and includes an expanded stent that is lodged against the blood vessel wall to inhibit movement of the stent and a distal electrode support. The expanded stent lumen is aligned with the electrode support lumen for allowing blood to flow through the aligned electrode support lumen and expanded stent lumen.

Another problem encountered in left heart stimulation is that conventional circumferential tip or ring electrodes on a coronary sinus lead will direct current in the direction of the adjacent epicardium but also in directions away from the targeted tissue, which may reduce stimulation efficiency. Stray current may also cause undesired extraneous stimulation, such as phrenic nerve stimulation or atrial stimulation during ventricular pacing. A coronary sinus lead would preferably direct current only in the direction of the targeted myocardium. Correctly positioning an endovascular lead having an electrode on only one side, however, would be difficult and time consuming.

Lead failure sometimes occurs when a conductor becomes fractured or the insulation between electrodes and/or conductors fails. A unipolar lead failure generally requires a surgical procedure to replace the failed lead. In the case of a bipolar lead, a bipolar stimulation or sensing configuration may be reprogrammed to unipolar if one electrode on the lead remains functional. However, the remaining functional electrode may be positioned at a different location relative to the targeted cardiac tissue and may not provide as effective or efficient sensing or stimulation as the bipolar pair. Furthermore, in some patients, unipolar sensing does not provide an acceptable signal-to-noise ratio.

For effective cardiac pacing, a delivered stimulation pulse must be of adequate energy to cause depolarization of the myocardium, referred to as "capture." The lowest pulse energy that successfully captures the heart is referred to as the pacing threshold. In order to verify that a pacing pulse has captured the heart, modern pacemakers are equipped with automatic capture detection algorithms. Capture may be verified by various methodologies known in the art such as sensing for an evoked R-wave or P-wave after delivery of a pacing pulse, sensing for the absence of an intrinsic R-wave or P-wave during the refractory period after a pacing pulse, or detecting a conducted depolarization in an adjacent heart chamber. Various capture verification methods are described in U.S. Pat. No. 5,601,615 issued to Markowitz et al., U.S. Pat. No. 5,324,310 issued to Greeninger et al., and U.S. Pat. No. 5,861,012 issued to Stroebel, each of which patents are incorporated herein by reference in their entirety. If capture is not verified, the pacing pulse energy may be automatically increased.

An electrode configuration used for pacing and evoked response sensing for capture detection may utilize a bipolar lead on which a tip electrode provides unipolar pacing and the tip and ring electrode pair provide bipolar sensing of the evoked response. A limitation of using the same electrode for pacing and evoked response sensing is that the pacing pulse and ensuing after-potential and electrode-tissue polarization artifact mask the evoked response until they dissipate, after which the evoked response, if any, has typically passed the sensing electrodes. Therefore, it is desirable to use an electrode pair that does not include the pacing electrode for sensing an evoked response. To overcome the problems of after-potential and the electrode-tissue polarization artifact, capture verification methods have been proposed which involves sensing for a conducted depolarization at a site away from the pacing electrode. For example, sensing a ventricular depolarization after an atrial pacing pulse has been delivered is evidence that the atrium was captured and the evoked depolarization was conducted to the ventricle.

For accurate evoked response detection, however, it is desirable to sense the evoked response using a bipolar sensing electrode pair in the vicinity of the stimulated cardiac tissue site. Unipolar sensing or sensing in other areas of the heart could lead to erroneous evoked response detection due to noise or other myopotentials being sensed as an evoked response. Furthermore, sensing for an evoked response in another area of the heart may not be possible in patients having conduction disorders.

What is needed, therefore, is an improved lead design that allows accurate targeting of excitable tissue in both endovascular and endocardial applications. A lead having an electrode arrangement that allows for reliable pacing and evoked response sensing for the purpose of capture verification is also desirable. Such a lead must be stabilized in a way that, when used endovascularly, does not cause undue vessel damage during fixation or repositioning and allows for unimpeded blood flow. Furthermore, an improved lead design should provide for alternative stimulation or sensing configurations without compromising effectiveness and efficiency of therapy delivery in case one electrode fails.

SUMMARY OF THE INVENTION

The present invention is directed to implantable electrical lead that includes an elongated lead body that extends between a proximal lead end and distal lead end, and a plurality of electrodes located along the distal lead end. An insulating material is positioned between each of the plurality of electrodes to electrically isolate each of the plurality of electrodes, and a plurality of insulated electrical conductors are each connected to a respective electrode of the plurality of electrodes. A microprocessor performs a threshold search corresponding to combinations of one or more electrodes of the plurality of electrodes to determine an optimal threshold, and selects the electrodes of the plurality of electrodes corresponding to the optimal threshold.

BRIEF DESCRIPTION OF THE DRAWINGS

Features and advantages of the present invention will be readily appreciated as the invention becomes better understood by reference to the following detailed description considered in connection with the accompanying drawings, in which like reference numerals designate like parts throughout.

DETAILED DESCRIPTION OF THE INVENTION

In the following detailed description, references are made to illustrative embodiments of medical leads adapted to be located in the heart or cardiac blood vessels in which aspects of the present invention may be implemented. It is understood that the invention may be practiced in other body implantable leads positioned for sensing or stimulating excitable tissue.

Figure 1:
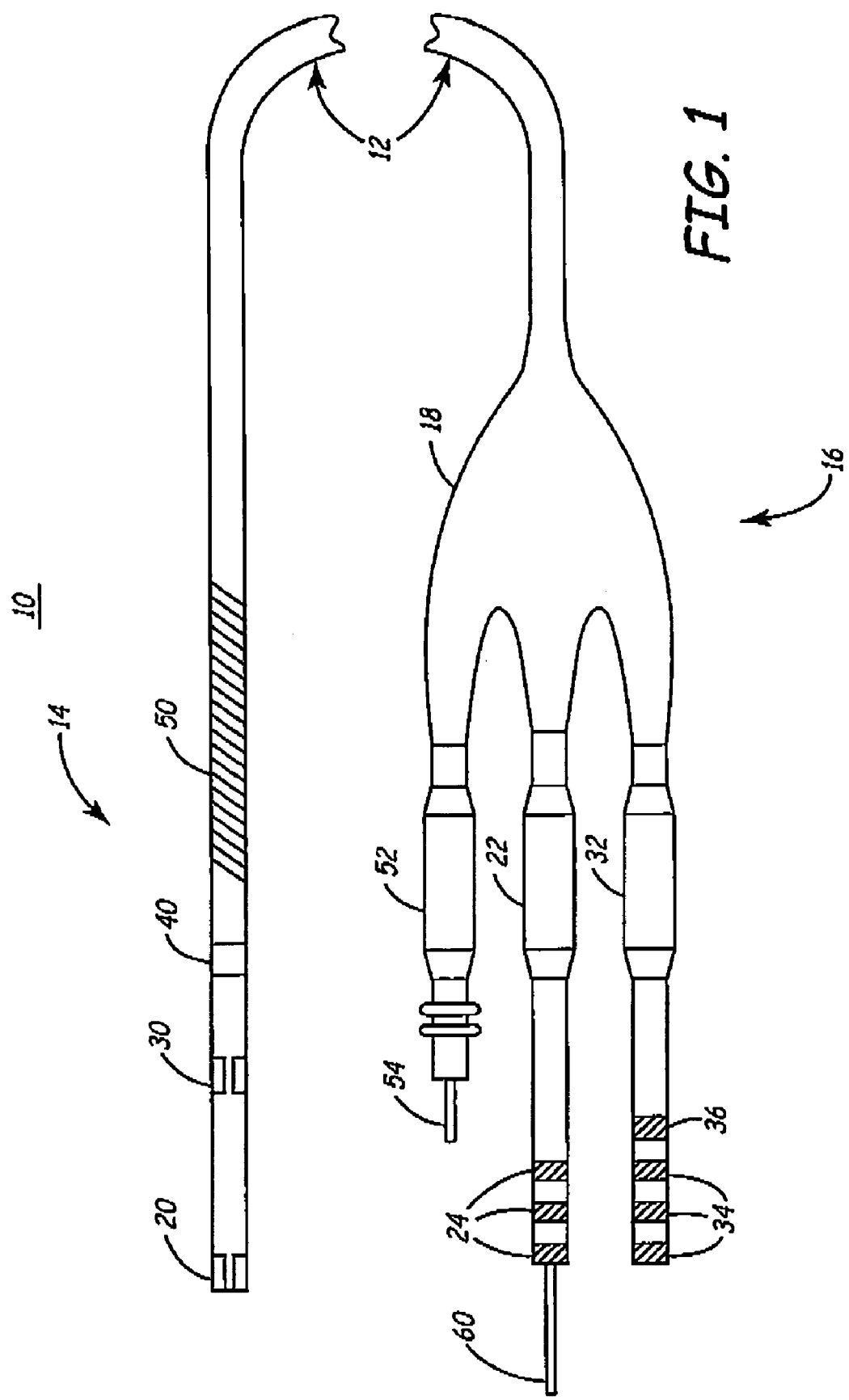
FIG. 1 is a plan view of an implantable electrical lead having a tip electrode array and a ring electrode array.

FIG. 1 is a plan view of a multipolar cardiac lead in accordance with an embodiment of the present invention. As illustrated in FIG. 1, a lead 10 according to the present invention includes an elongated lead body 12 having a connector assembly 16 at a proximal end adapted for connecting to an implantable device, such as an ICD, and an electrode head assembly 68 at a distal end 14 for carrying one or more electrodes. Lead 10 is shown having, at or near distal end 14, a tip electrode array 20, a ring electrode array 30, a ring electrode 40, and a defibrillation coil electrode 50. The tip electrode array 20 and the ring electrode array 30 each include multiple electrodes, for example three electrodes, separated by insulating material. Electrodes within the tip electrode array 20 and/or ring electrode array 30 and/or ring electrode 40 may be utilized to sense cardiac signals and/or deliver pacing pulses to a patient's heart. The defibrillation coil electrode 50 is used for delivery of a defibrillation shock as a result of a detected tachycardia or fibrillation condition.

The lead body 12 takes the form of an extruded tube of biocompatible plastic such as silicone rubber. The lead body 12 includes multiple lumens for carrying multiple insulated conductors from the connector assembly 16 to the corresponding electrodes arrays 20 and 30 and electrodes 40 and 50 located at or near the distal lead end 14. The multi-lumen lead body 12 may correspond generally to that disclosed in U.S. Pat. No. 5,584,873 issued to Shoberg et al., incorporated herein by reference in its entirety. Two of the insulated conductors carried by lead body 12 may be stranded or cabled conductors, each electrically coupled to one of the ring electrode 40 and the defibrillation coil 50. The cabled conductors may correspond generally to the conductors disclosed in U.S. Pat. No. 5,246,014, issued to Williams et al., incorporated herein by reference in its entirety. A third and fourth conductor are preferably multi-filar coiled conductors, for example of the type described in U.S. Pat. No. 4,922,607 issued to Doan et al., incorporated herein by reference in its entirety. Each filar of the multi-filar coiled conductors is coupled to an individual electrode within the tip electrode array 20 or the ring electrode array 30. The filars are electrically insulated from each other for example by polytetrafluoroethylene (PTFE) or ethyl tetrafluoroethylene (ETFE) tubing.

The connector assembly 16 includes multiple connector extensions 22, 32, and 52 arising from a trifurcated connector sleeve 18, typically formed of silicone rubber. The connector extensions 22, 32 and 52 couple the lead 10 to an implantable medical device such as an implantable cardioverter defibrillator (ICD).

Connector extension 22 is shown as a tri-polar connector including three connector rings 24. Connector extension 22 houses a multi-filar coiled conductor of which each filar is electrically coupled at a proximal end to one of the connector rings 24 and at a distal end to one of the three electrodes included in tip electrode array 30. A stylet 60 may be advanced within an inner lumen of the coiled conductor carried by connector extension 22 toward the distal end of the lead 10 to aid in lead placement during an implant procedure.

Connector extension 32 is shown as a quadrapolar connector including three connector rings 34 and a fourth connector ring 36. The three connector rings 34 are electrically coupled to individual filars within a multi-filar coiled conductor extending to the ring electrode array 30. The distal end of each filar is coupled to one of three electrodes included in ring array 30. The fourth connector ring 36 is coupled to an insulated cabled conductor that extends to ring electrode 40.

Connector extension 52 carries a single connector pin 54 that is electrically coupled to an insulated cable extending the length of the lead body 12 and electrically coupled to the defibrillation coil electrode 50. While the lead 10 depicted in FIG. 1 is a multi-polar pacing and defibrillation lead, aspects included in the invention may be practiced in any unipolar, bipolar, or multi-polar lead by providing at least one tip or ring electrode array. One or more electrode arrays may be provided alone or with any combination of conventional tip, ring or coil electrodes.

Figure 2:
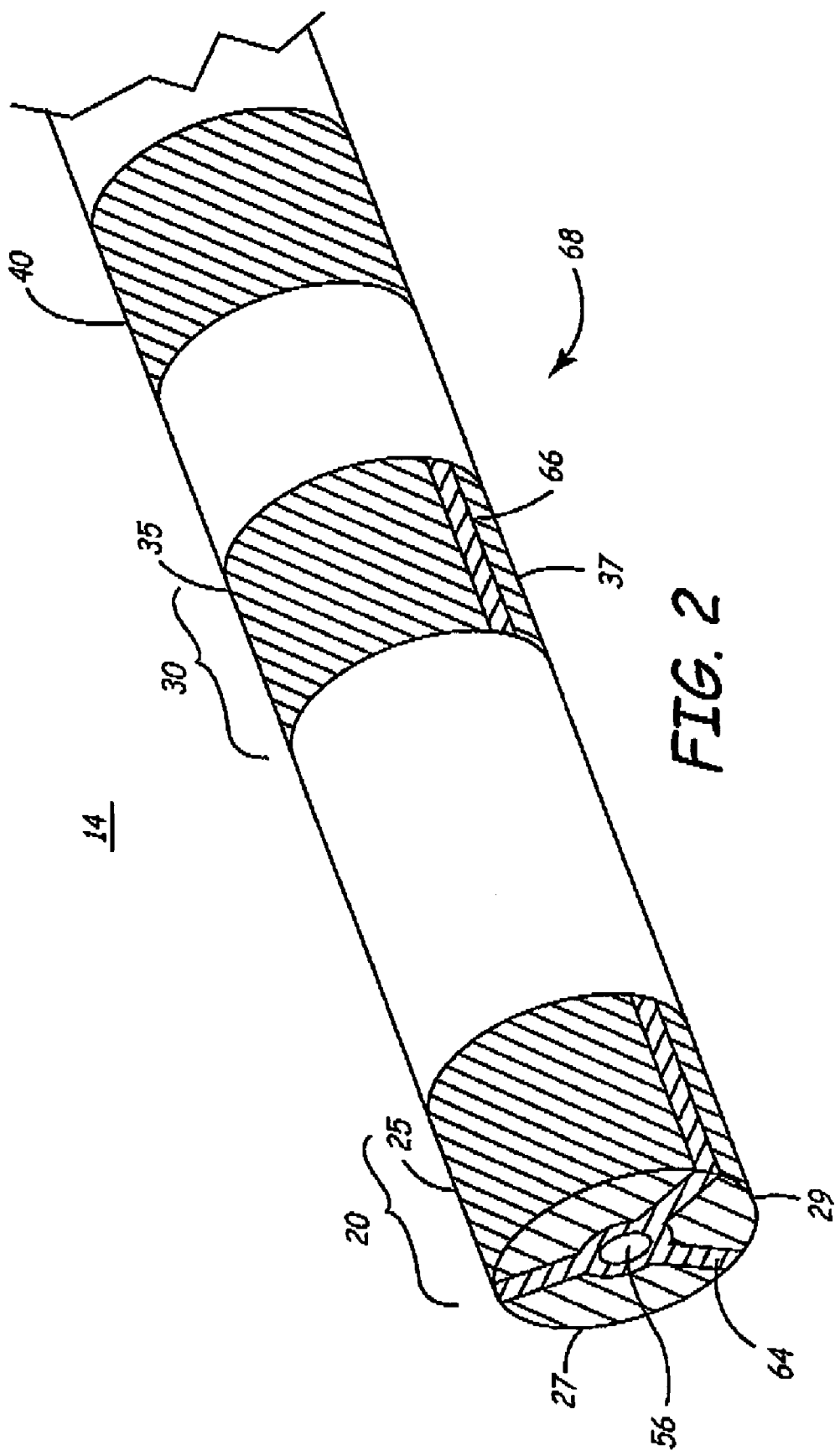
FIG. 2 is a perspective view of a distal end of the lead shown in FIG. 1.

FIG. 2 is an enlarged, perspective view of the electrode head assembly 68 located at the distal lead end 14 shown in FIG. 1. The tubular electrode head assembly 68 is preferably fabricated from a relatively rigid biocompatible polymer, such as polyurethane. As illustrated in FIG. 2, tip electrode array 20, mounted on the tip of the electrode head assembly 68, includes three approximately equally sized electrodes 25, 27 and 29 arranged circumferentially with respect to the electrode assembly 68. The tip electrode array 20 could alternatively comprise two or more electrodes of approximately equal or unequal sizes. The electrodes 25, 27 and 29 are preferably platinum iridium electrodes, but may be manufactured from any acceptable, medical grade, conductive biomaterial. A layer of insulating material 64, such as ceramic, is arranged radially with respect to the electrode head assembly 68, between each of the electrodes 25, 27 and 29 such that the electrodes 25, 27 and 29 within the array 20 are electrically insulated from each other.

The insulator 64 optionally provides a center port 56. When the electrode array 20 is used as a tip electrode, as shown in FIG. 1, the port 56 may be used to hold a pharmaceutical agent. The pharmaceutical agent, which may be an anti-inflammatory, antibiotic, or other agent, may be added as a powdered form to a polymer adhesive that is injected into port 56 such that the agent elutes from the polymer over time after implantation. In one embodiment, the port 56 holds a steroid powder added to medical grade silicone adhesive, which when released after implantation will minimize the inflammatory tissue response around the electrode array 20. Various embodiments for providing a drug dispenser in an electrical medical lead that may be used in conjunction with the present invention are disclosed in U.S. Pat. No. 4,711,251 issued to Stokes, incorporated herein by reference in its entirety.

Figure 3:
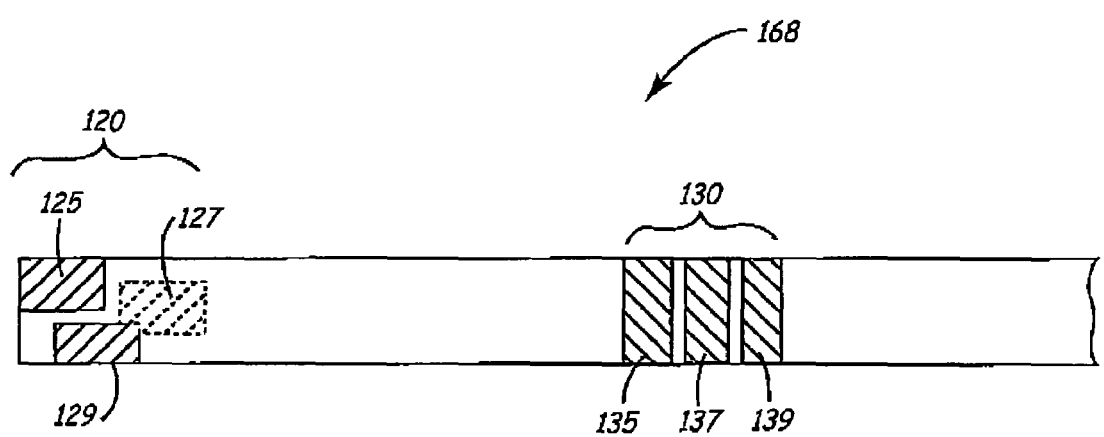
FIG. 3 is a plan view illustrating alternative arrangements of electrodes within an electrode array according to the present invention.

In the same way, the ring electrode array 30 includes three, approximately equally-sized, circumferentially arranged electrodes separated from each other by a layer of insulating material 66. FIG. 3 illustrates alternative arrangements of electrodes within an electrode array. In the alternative tip electrode 120, three electrodes 125, 127, and 129 are arranged circumferentially around the electrode head assembly 68 but staggered along its length such that electrode 125 is located at the distal lead tip, electrode 129 is located slightly proximal to electrode 125, and electrode 127 is slightly proximal to electrode 129. This staggered arrangement could equally be applied to a ring electrode array.

The ring electrode array 130 shown in FIG. 3 includes three ring electrodes 135, 137, and 139, each encircling electrode head assembly 68 and spaced at close intervals longitudinally with respect to each other along the electrode head assembly 68. This longitudinally-spaced ring arrangement could also be applied to a tip electrode array. It is recognized that numerous variations of electrode array arrangements may exist in which two or more electrodes are arranged in close proximity to each other.

Figure 4:
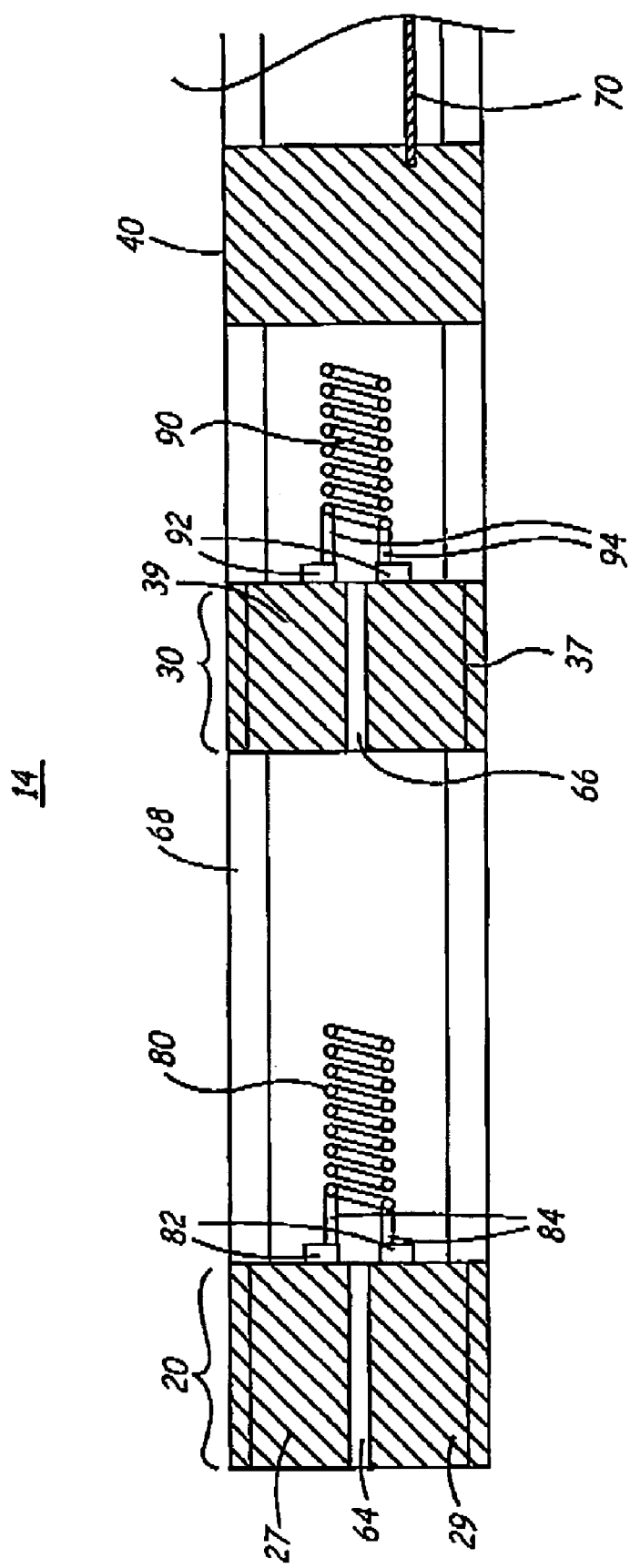
FIG. 4 is a side, cut-away view of the distal lead end shown in FIG. 2.

FIG. 4 is a side cut-away view of the tubular electrode head assembly 68 of the lead 10 shown in FIG. 2. Electrodes 27 and 29 included in tip array 20 are visible in this view, and electrodes 37 and 39 of ring array 30 are visible in this view. Electrodes 27 and 29 included in tip array 20 are each provided with connection tabs 82 to allow electrical coupling, for example by laser welding, to individual filars 84 included in the multi-filar coiled conductor 80. Multi-filar conductor 80 is connected at a proximal end to connector rings 24 (FIG. 1). Insulation material 64 is shown between electrodes 27 and 29.

Electrodes 37 and 39 included in ring array 30 are each provided with connection tabs 92 to allow electrical coupling to individual filars 94 included in the multi-filar coiled conductor 90. Multi-filar conductor 90 is connected at its proximal end to connector rings 34 (FIG. 1). Ring electrode 40 is shown coupled to cabled conductor 70, which is further coupled at its proximal end to connector ring 36. By providing separate, insulated conductors to each of the insulated electrodes 25, 27, 29 of tip array 20 and 35, 37 and 39 of ring array 30, the electrodes 25, 27, 29, 35, 37 and 39 may be selected individually or in any combination for pacing and/or sensing functions.

Figure 5:
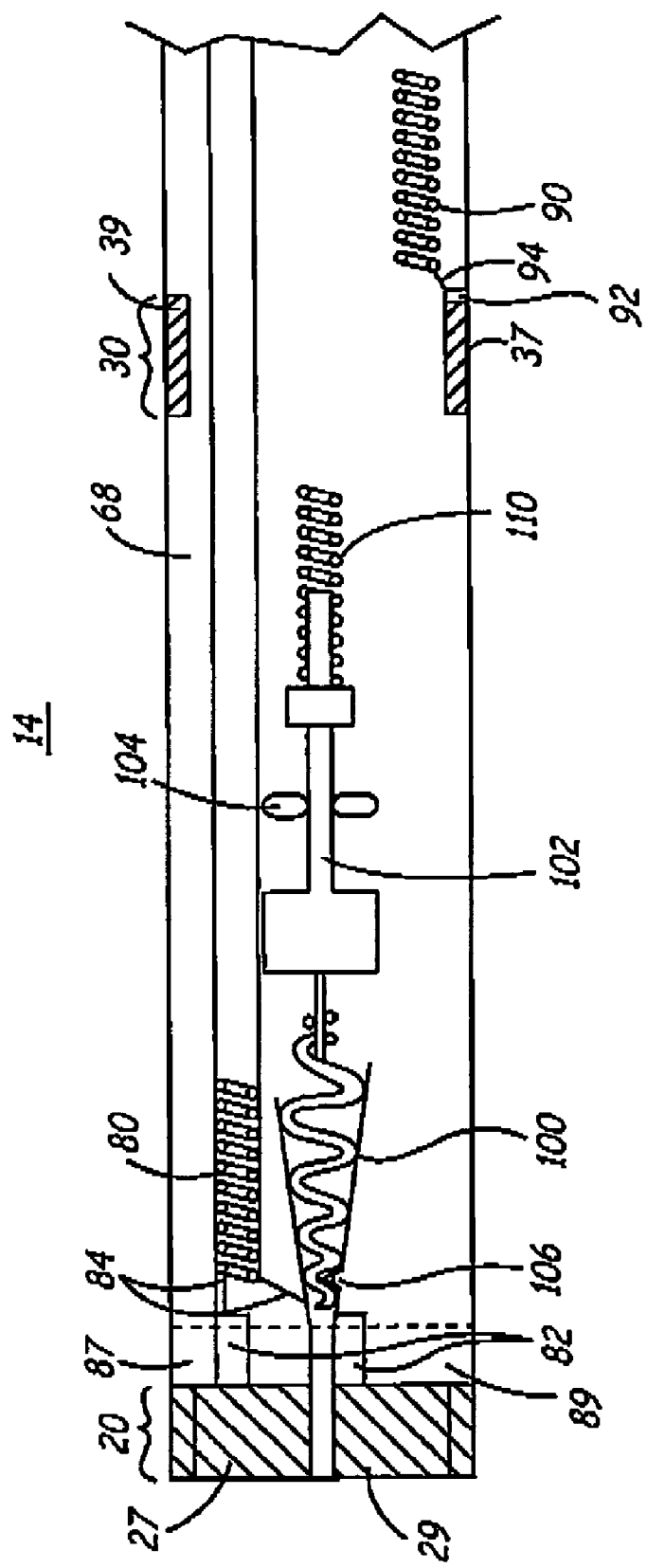
FIG. 5 is a side, cut-away view of a distal lead end of an implantable electrical lead having a helical expansion member for expanding a tip electrode array.

An alternative embodiment of the lead 10 is shown by the side cutaway view of FIG. 5. In this embodiment, the tip electrode array 20 is expandable. The electrodes 27 and 29 within array 20 are mounted on flexible electrode extensions 87 and 89, respectively. An expansion member for expanding the flexible electrode extensions 87 and 89 takes the form of a conically-shaped helix 100. The helix 100 may function exclusively as an expansion member, in which case the helix may be formed from any relatively rigid biocompatible polymer, such as urethane, or a biocompatible metal. The tip of helix 100 may be blunted to prevent unintentional tissue damage. In other embodiments, the helix 100 may also serve as an additional electrode for cardiac pacing and/or sensing. When used as an electrode, the helix 100 is formed from a conductive biocompatible metal such as platinum iridium alloy. The helix 100 may also serve as an active fixation device for anchoring the lead 10 in a desired position for additional stability. In this case, the helix 100 has a sharpened tip for securing the helix 100 in tissue. Reference is made to U.S. Pat. No. 4,217,913 issued to Dutcher, incorporated herein by reference in its entirety.

The helix 100 is shown in FIG. 5 to be mounted on a drive shaft 102 that is further connected to a rotatable coil 110. The coil 110 extends the length of the lead body 12 and may be coupled to a connector pin provided on one of the connector extensions of connector assembly 16. During a lead implant or explant procedure, a physician may rotate such a connector pin relative to the connector assembly 16 causing advancement or retraction of the helix 100 in a manner generally described in U.S. Pat. No. 4,106,512 to Bisping et al., incorporated herein by reference in its entirety. Rotation of the connector pin rotates the drive shaft 102 via the coil 110. As the drive shaft 102 is rotated, the helix 100 is actuated by a guide 106 such that the helix 100 is advanced toward the lead end. A drive shaft seal 104 is optionally provided to prevent the ingress of body fluids into the lumen of lead 10.

Figure 6:
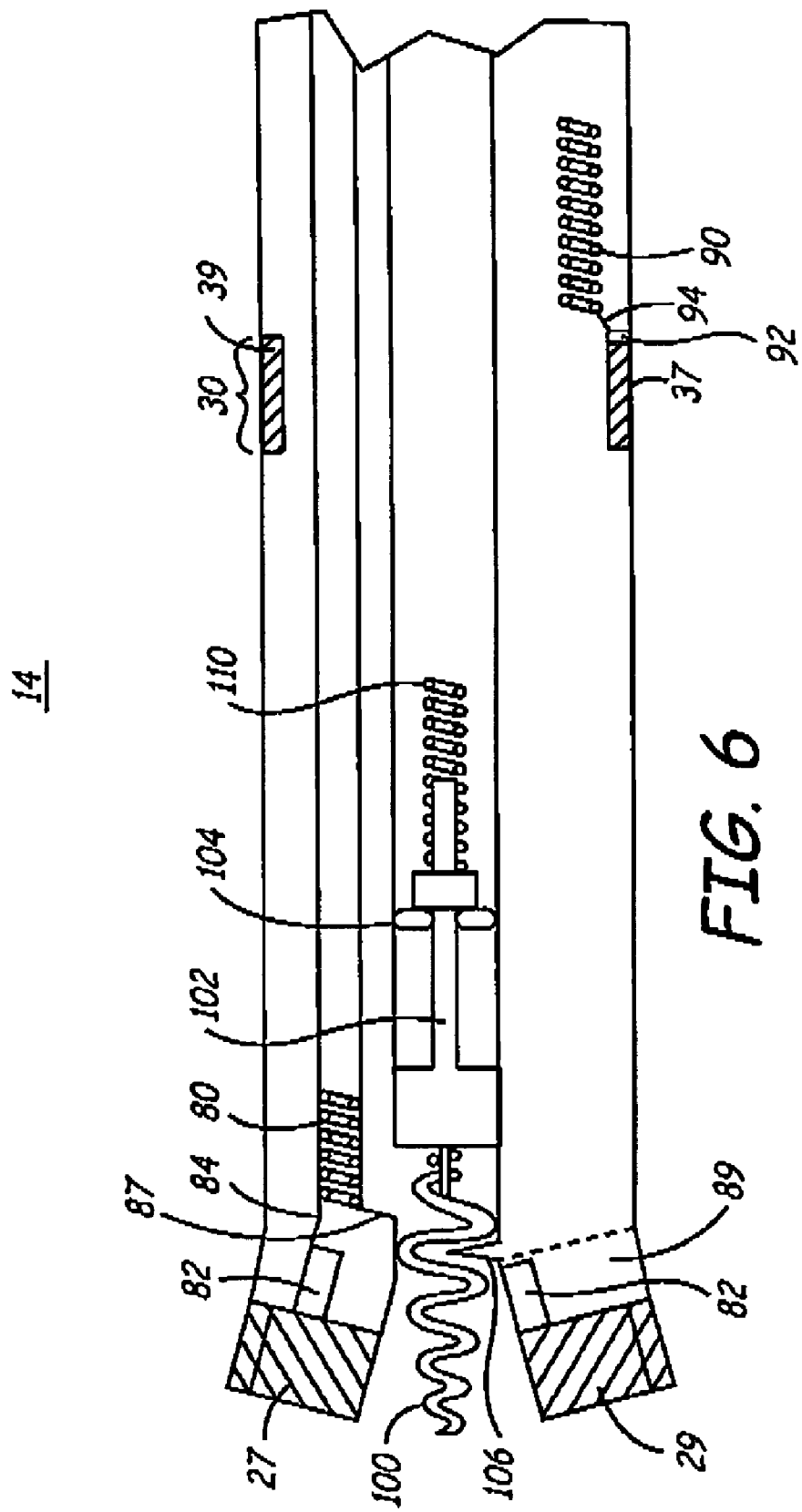
FIG. 6 is a side cut-away view of the distal lead end shown in FIG. 5 showing a tip electrode array in a fully expanded position.

In FIG. 6, the tip electrode array 20 is shown in a fully expanded position. The helix 100 is in an advanced position such that the widest portion of the conical helix 100 has caused the flexible electrode extensions 87 and 89, each carrying one of the electrodes 27 and 29 included in tip array 20, to bend outward.

Expansion of the tip array 20 in this way provides a passive fixation mechanism for stabilizing the lead position. When used as an endocardial electrode, the expanded electrode array 20 may engage with the endocardial trabeculae, holding the distal lead end in place. If the initial lead position does not result in acceptable pacing or sensing thresholds, the helix 100 may be retracted, contracting the tip array 20, to allow easy removal and lead repositioning. This reversible fixation mechanism is particularly useful when the lead 10 is used as an endovascular lead. Contraction of the tip array 20 allows easy retraction of the lead within a narrow vein without undue damage to vessel walls or vein valves. Furthermore, the expanded electrode array provides stable lead positioning within a blood vessel without blocking the flow of blood or puncturing the blood vessel walls.

Another advantage of expanding the tip electrode array 20 relates to the benefit of increasing the inter-electrode distance when the tip array 20 is used for pacing and evoked response sensing. If, for example, one electrode of tip array 20 is used for pacing in a unipolar configuration with a device housing or in a bipolar configuration with any of ring electrode array 30 or ring electrode 40, the remaining two electrodes within tip array 20 are available for sensing an evoked response in the same vicinity of the delivered pacing pulse. Sensing for an evoked response at the site of stimulation delivery enables accurate capture detection since other myopotentials, which may be present at more remote sensing sites, are less likely to interfere with evoked response sensing. By using electrodes different than the electrode used for pacing, problems associated with post-pace polarization artifacts can be avoided. The increased inter-electrode distance in an expanded tip array further enhances the ability to sense the evoked response using electrodes within the same array because the post-pace polarization artifact will diminish as the distance from the placing electrode increases.

Figure 7:
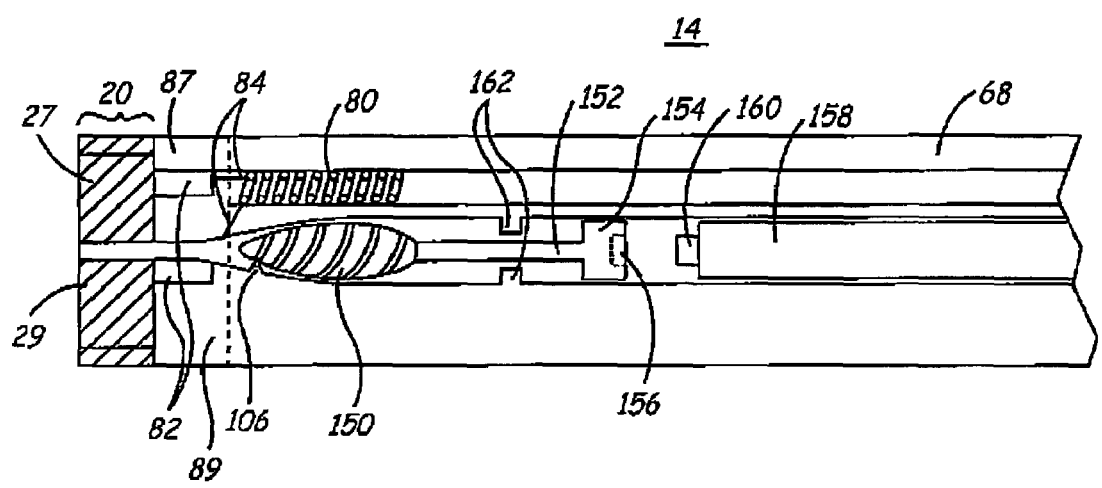
FIG. 7 is a side, cut-away view of a distal lead end having an alternative expansion member for expanding a tip electrode array according to the present invention.

An alternative embodiment of an expansion member is shown in FIG. 7. In this embodiment, the expansion member takes the form of a grooved cone 150, which is preferably fabricated from a biocompatible, relatively rigid polymer such as polyurethane. The cone 150 is mounted on a drive shaft 152 having a screw-like head 154 with a slot 156. A stylet 158 having a screw driver-like blade 160 mounted on its distal end may be advanced within a lumen of the lead body 12. The blade 160 may be inserted into slot 156 and, upon rotation of the stylet 158 at its proximal end, cause rotation of the drive shaft 152. When the drive shaft 152 is rotated, the cone 150 is actuated by the guide 106 and is advanced toward the distal lead tip to cause expansion of the tip electrode array 20 mounted on flexible electrode extensions 87 and 89.

In one embodiment, the expansion member may be coated with a substrate or solvent carrying a pharmaceutical agent, such as an anti-inflammatory drug. The expansion member may be dip-coated in a solvent, such as acetone, in which a steroid has been dissolved. The steroid will elute from the coating over time after implantation and prevent a hyperinflammatory response at the implant site. A method for treating an electrode with a steroid solution, which may be adapted for use in the present invention for treating the expansion member, is generally described in U.S. Pat. No. 5,987,746 issued to Williams, incorporated herein by reference in its entirety.

Figure 8:
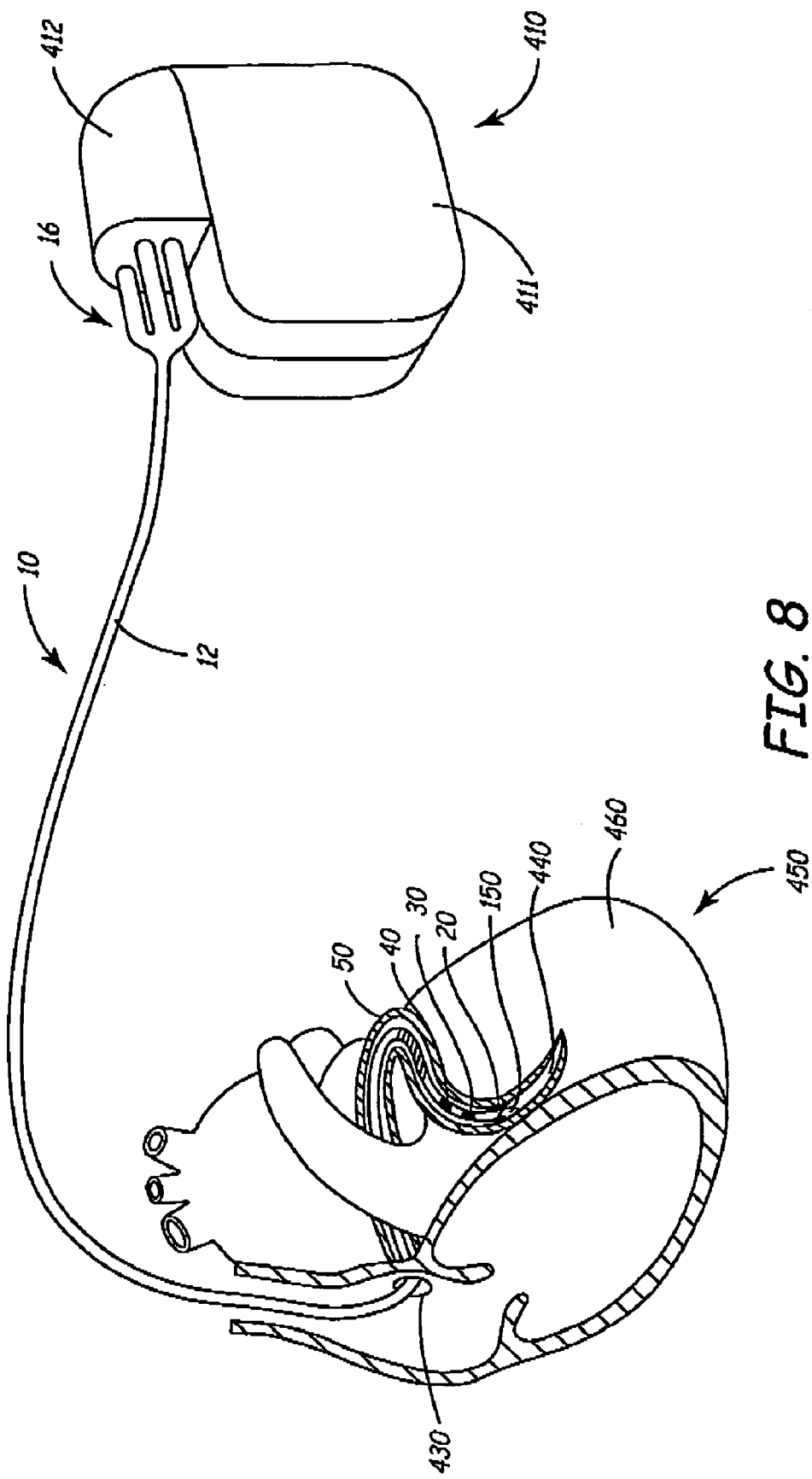
FIG. 8 is an illustration showing the lead of FIG. 1 implanted within the coronary vessels of a patient's heart via the coronary sinus and in communication with an implantable cardioverter defibrillator, according to a preferred embodiment of the present invention.

In FIG. 8, the lead 10 is shown as a part of a cardiac stimulation system including an ICD 410 coupled to a patient's heart 450 by way of lead 10. The ICD 410 is encased in a housing 411 and provided with a connector block 412 to accommodate connection of lead 10 to the ICD 410. The heart 450 is shown with a partially open view revealing the coronary sinus 430. The lead 10 is advanced within the vasculature of the left side of the heart via the coronary sinus and great cardiac vein. A tip electrode array 20 is disposed in a vascular lumen 440 adjacent the left ventricle 460. The tip electrode array is shown in an expanded position at a desired cardiac implantation site. A blunted expansion cone 150 has been advanced in order to expand the electrodes within array 20 against the walls of lumen 440 so as to provide better electrode contact with the epicardial tissue and to stabilize the position of the lead 10 as previously described in conjunction with FIG. 7. The coronary sinus lead 10 is also equipped with a ring electrode array 30, a ring electrode 40 and a defibrillation coil electrode 50. The coronary sinus lead 10 is shown connected to the ICD 410 via the trifurcated connector assembly 16, which accommodates connection of ICD circuitry to the conductors within lead body 12 and their respective electrodes.

Figure 9:
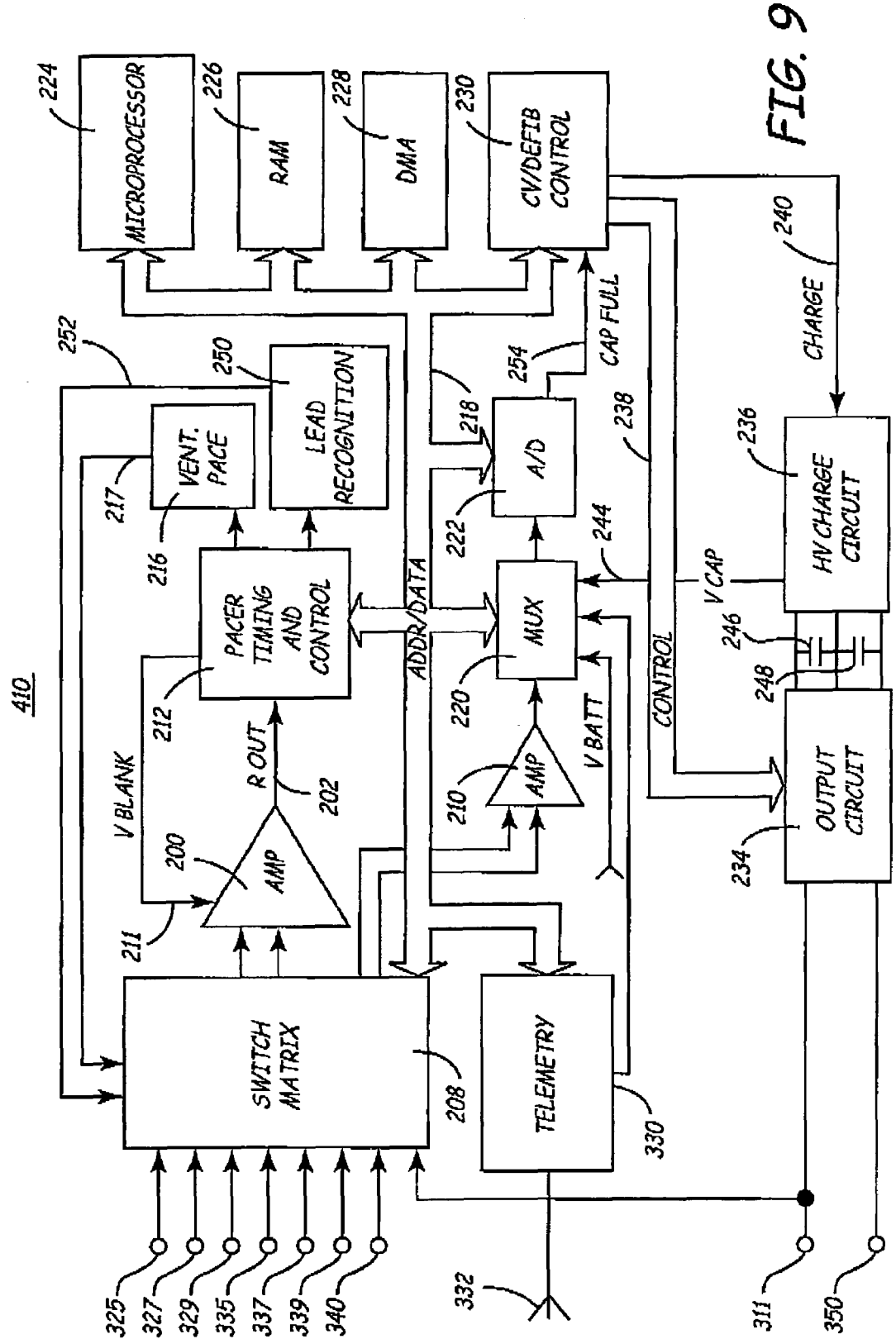
FIG. 9 is a functional, block diagram of the implantable cardioverter defibrillator (ICD) shown in FIG. 8.

A functional schematic diagram of the ICD 410 is shown in FIG. 9. This diagram should be taken as exemplary of one type of device within a body implantable system that includes a lead having one or more electrode arrays in accordance with the present invention. The disclosed embodiment shown in FIG. 9 is a microprocessor-controlled device, but the methods of the present invention may also be practiced in other types of devices such as those employing dedicated digital circuitry.

With regard to the electrode system illustrated in FIG. 8, the ICD 410 is provided with a number of connection terminals for achieving electrical connection to the lead 10 via the connector assembly 16 and the respective electrodes via their associated conductors. The connection terminal 311 provides electrical connection to the housing 411 for use as the indifferent electrode during unipolar stimulation or sensing. The connection terminal 350 provides electrical connection to the defibrillation coil electrode 50. The connection terminals 311 and 350 are coupled to the high voltage output circuit 234 to facilitate the delivery of high energy shocking pulses to the heart using the defibrillation coil electrode 50 and housing 411.

The connection terminals 325, 327 and 329 provide electrical connection to the electrodes 25, 27 and 29, respectively, within tip electrode array 20. The connection terminals 335, 337 and 339 provide electrical connection to the electrodes 35, 37 and 39, respectively, within ring electrode array 30. The connection terminal 340 provides electrical connection to the ring electrode 40. The connection terminals 325, 327, 329, 335, 337, 339, and 340 are further coupled to a switch matrix 208.

Switch matrix 208 is used to select which of the available electrodes are coupled to a ventricular sense amplifier (AMP) 200 for sensing ventricular signals. Selection of the electrodes is controlled by the microprocessor 224 via data/address bus 218. The selected electrode configuration may be varied according to the various sensing, pacing, cardioversion and defibrillation functions of the ICD 410.

The ventricular sense amplifier 200 preferably takes the form of an automatic gain controlled amplifier with adjustable sensing thresholds. The general operation of the ventricular sense amplifier 200 may correspond to that disclosed in U.S. Pat. No. 5,117,824 issued to Keimel et al., incorporated herein by reference in its entirety. Whenever a signal received by the ventricular sense amplifier 200 exceeds a ventricular sensing threshold, a signal is generated on the R-out signal line 202.

Switch matrix 208 is also used to select which of the available electrodes are coupled to a wide band amplifier 210 for use in digital signal analysis. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. Received telemetry is provided to microprocessor 224 via multiplexer 220. Numerous types of telemetry systems known for use in implantable devices may be used.

The remainder of the circuitry illustrated in FIG. 9 is an exemplary embodiment of circuitry dedicated to providing cardiac pacing, cardioversion and defibrillation therapies. The pacer timing and control circuitry 212 includes programmable digital counters, which control the basic time intervals associated with various pacing modes or antitachycardia pacing therapies delivered in the ventricle. Pacer circuitry 212 also determines the amplitude of the cardiac pacing pulses under the control of microprocessor 224.

During pacing, escape interval counters within pacer timing and control circuitry 212 are reset upon sensing of R-waves as indicated by signals on Rout signal line 202. The durations of the escape intervals are determined by microprocessor 224 via data/address bus 218. The value of the count present in the escape interval counters when reset by sensed R-waves can be used to measure R-R intervals for detecting the occurrence of a variety of arrhythmias. In accordance with the selected mode of pacing, if the ventricular escape interval expires pacing pulses are generated by ventricular pacer output circuit 216. The pacer output circuit 216 is coupled to the desired pacing electrodes via switch matrix 208 along signal line 217. The escape interval counters are reset upon generation of pacing pulses, and thereby control the basic timing of cardiac pacing functions, including antitachycardia pacing. When a pacing pulse is delivered, a signal is generated by pacer timing and control 212 on blanking signal line (V BLANK) 211 to prevent saturation of the sense amplifier 200 during the pacing pulse.

Thus, complete programmability of the electrodes used in pacing and/or sensing is possible via switch matrix 208. Any of the electrodes included in tip array 20, ring electrode array 30 and ring electrode 40 may be selected individually or in any combination as the anode for unipolar pacing with the ICD housing 411 serving as the cathode. For bipolar or multi-polar electrode configurations, the electrodes within tip array 20, ring array 30 and ring electrode 40 may be selected in any combination. For example, one or more of the electrodes within an array may be selected to serve as an anode with any or all of the remaining electrodes in the same array selected as the cathode. Alternatively, electrodes may be selected from one array 20 or 30 to serve as the anode and from the other array to serve as the cathode. Electrodes within arrays 20 or 30 may also be selected to function with ring electrode 30 in a bipolar configuration.

The ICD 410 is preferably equipped with a capture detection algorithm executed under the control of microprocessor 224. Following delivery of a pacing pulse by ventricular pacer output circuit 216, a desired pair of electrodes may be selected via switch matrix 208 to sense for the evoked response. If an evoked response is not detected, the pacing pulse amplitude may be adjusted by pacer circuitry 212 under the control of microprocessor 224. Exemplary circuitry for detecting an evoked response is described in previously incorporated U.S. Pat. No. 5,601,615 issued to Markowitz et al., U.S. Pat. No. 5,324,310 issued to Greeninger et al., and U.S. Pat. No. 5,861,012 issued to Stroebel.

Pacer timing and control circuitry 212 is coupled to lead recognition circuit 250 for determining availability of pacing or sensing paths. The lead recognition circuit 250 may include impedance measuring circuitry such that valid lead pathways may be identified when a measured impedance between electrodes falls within an acceptable range. Lead recognition circuit 250 is coupled to possible electrode configurations via switch matrix 208 along signal line 252. A lead recognition apparatus and method that may be used in ICD 410 is generally described in U.S. Pat. No. 5,534,018 issued to Wahistrand et al., incorporated herein by reference in its entirety.

The microprocessor 224 includes associated ROM in which stored programs controlling the operation of the microprocessor 224 reside. A portion of the memory 226 may be configured as a number of recirculating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microcontroller 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CAP FULL) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

Figure 10:
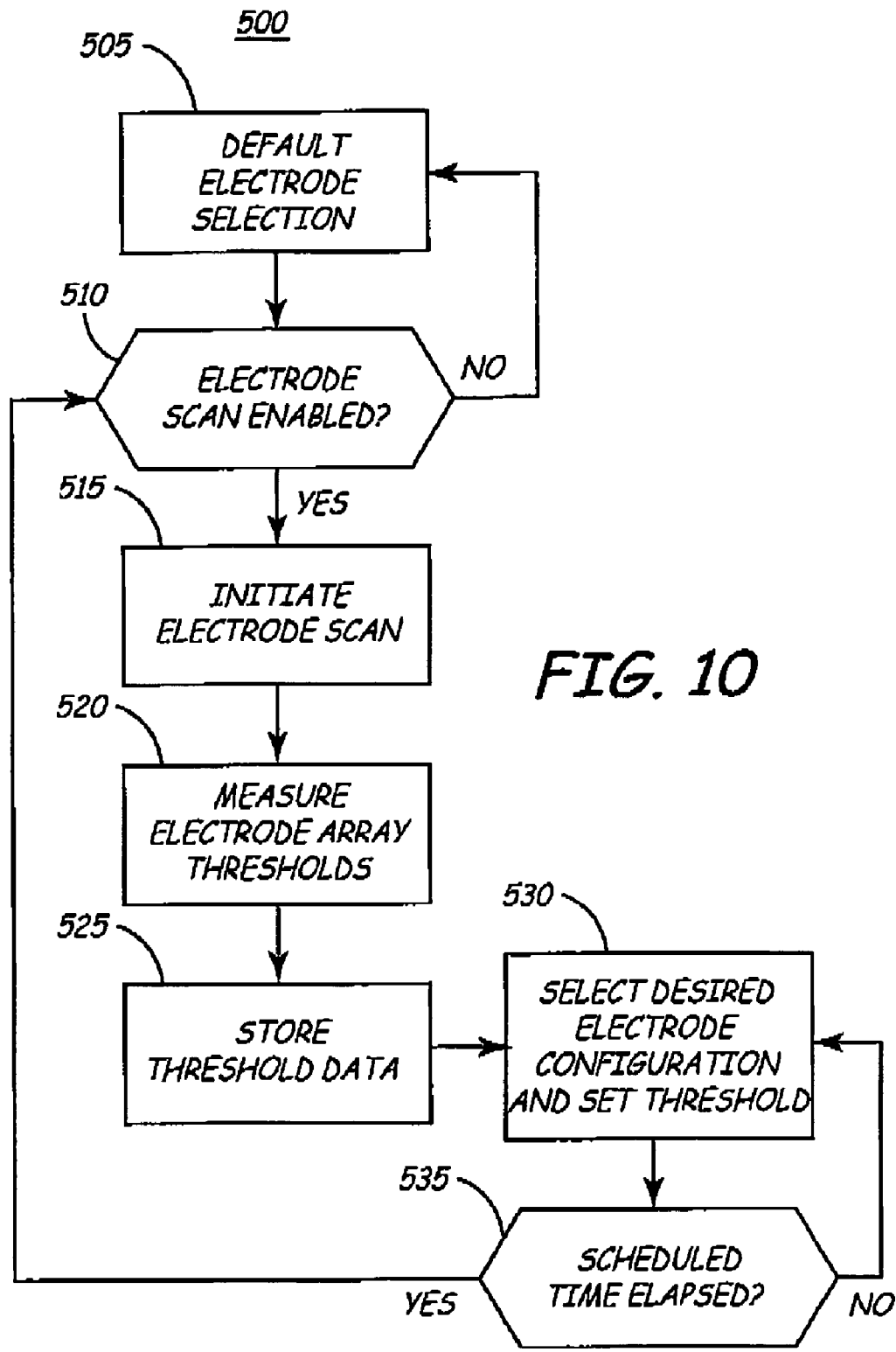
FIG. 10 is a flow chart of a method for using the lead shown in FIG. 8 in conjunction with the implantable cardioverter defibrillator (ICD) of FIG. 9.

The flow chart shown in FIG. 10 is an overview of one method for using the lead 10 in conjunction with the ICD 410. Although a single chamber, left-ventricular device is depicted in FIGS. 8 and 9, a lead having one or more electrode arrays could be used with atrial or ventricular single chamber devices, with dual chamber devices or multichamber devices. These devices may be any of implantable or temporary pacemakers, ICDs or cardiac monitoring systems. Other than cardiac stimulation or monitoring systems, the lead 10 and the method 500 of FIG. 10 to be described may also be used in implantable or temporary neurostimulators or other medical devices used for stimulating and/or sensing excitable tissue.

In regard to the implantable system illustrated in FIG. 8 and the ICD 410 shown in FIG. 9, the method 500 shown in FIG. 10 is preferably performed under the control of microprocessor 224. Method 500 allows the microprocessor 224 to automatically determine which of the electrodes included in an electrode array provide the optimal stimulation or sensing configuration by performing an electrode scan. During the electrode scan, the pacing and/or sensing thresholds of the available electrode combinations is measured. Additionally, electrode lead impedance may be measured. The optimal stimulation configuration is determined as the electrode or combination of electrodes resulting in the lowest pacing threshold that successfully captures the targeted tissue without depolarizing non-targeted tissue. For example, in the embodiment shown in FIG. 8, left ventricular capture is desired without atrial capture or phrenic nerve stimulation. An optimal sensing configuration may be identified as the electrode configuration resulting in the highest signal amplitude or signal-to-noise ratio. For the left ventricular application of FIG. 8, the optimal sensing configuration would provide the highest R-wave amplitude or the greatest R-wave signal-to-noise ratio.

When the method 500 begins at step 505, the electrode configuration selected is a default configuration. Typically, the default configuration is the simultaneous selection of all the electrodes included in an electrode array. This default configuration will be used for designated pacing or sensing functions until a more optimal configuration is identified. For example, electrodes 25, 27 and 29 may be selected simultaneously to serve as the anode during unipolar pacing as the default pacing configuration. A default sensing configuration may be set as the bipolar combination of the simultaneously selected tip array electrodes 25, 27 and 29 paired with the simultaneously selected ring array electrodes 35, 37 and 39.

At decision step 510, the microprocessor 224 determines if an electrode scan is enabled. The electrode scan feature is preferably enabled or disabled by a physician using an external programmer in telemetric communication with the ICD 410. If the electrode scan is disabled, the electrode selection remains in the default configuration. Alternatively, a physician may manually program an electrode configuration to override the default selection.

If the electrode scan is enabled, a scan is initiated at step 515. An electrode scan may be initiated by any of a number of triggering events. Upon implantation of the lead 10 and ICD 410, a detection of valid electrode pathways by lead recognition circuitry 250 may trigger the initiation of the electrode scan at step 515. Other triggering events for an electrode scan may include detection of a lead failure or a change in lead status. Reference is made to previously incorporated U.S. Pat. No. 5,534,018 and to U.S. Pat. No. 6,317,633 issued to Jorgenson et al., incorporated herein by reference in its entirety. A scan may also be triggered manually, on a scheduled or periodic basis, or in response to a loss of capture.

At step 520, the microprocessor 224 performs a threshold search on each electrode within an array individually and in any number of desired combinations. A threshold search may be performed according to methods known in the art. For example, a threshold search may be performed by successively reducing the pacing pulse amplitude until capture is lost. For an exemplary threshold search algorithm, reference is made to U.S. Pat. No. 3,757,792 issued to Mulier, incorporated herein by reference in its entirety.

In regard to the electrode configuration shown in FIG. 8, electrodes 25, 27 and 29 in tip electrode array 20 and electrodes 35, 37, and 39 in ring electrode array 30 may be selected in any unipolar, bipolar or multipolar configuration. For each configuration selected, the left ventricular pacing threshold and/or the R-wave sensing threshold is measured and stored in memory at step 525. After measuring and storing the thresholds for all desired electrode configurations, the configuration yielding the optimal threshold is selected via switch matrix 208 at step 530 to operate as the designated configuration for the associated pacing or sensing function. The pacing pulse energy and/or the sensing threshold may also be set at step 530 according to the stored threshold for the selected electrode configuration.

An electrode scan may be performed automatically as described or semi-automatically under the supervision of a clinician such that observation of any extraneous stimulation or undersensing or oversensing may be made. Final selection of the optimal electrode configuration may then be made manually to eliminate electrode configurations producing extraneous stimulation or inaccurate sensing.

At decision step 535, the microprocessor 224 determines if a preset amount of time, for example 24 hours, has elapsed. Once this time is elapsed, an electrode scan may be automatically repeated. Threshold changes may occur over time as electrodes become encapsulated by fibrotic scar tissue or with changes in a patient's physiologic condition, the use of drugs, or changes in disease state. By repeating the electrode scan periodically, the optimal electrode configuration and appropriate pacing energy or sensing threshold settings may be updated in response to such changes.

The present invention is realized in an implantable medical lead possessing one or more electrode arrays, each comprising multiple electrodes that are electrically insulated from each other. The electrodes within an array are preferably arranged circumferentially in relation to the lead body and may be located substantially in the area normally occupied by a conventional tip or ring electrode.

A lead provided by the present invention includes a lead body extending between a proximal lead end and distal lead end for carrying multiple, insulated conductors. The conductors are each electrically coupled to an associated electrode at or near the distal lead end and to connectors at the proximal lead end for establishing connection to an implantable medical device. The lead may be equipped with a tip electrode array and/or one or more ring electrode arrays comprising two or more, preferably three, electrodes each. The electrodes within an array may be spaced from each other around the circumference of the lead and/or along its length. The electrodes within an array are electrically insulated from each other by nonconductive material, such as a ceramic, layered between each electrode in the array.

In one embodiment, a tip electrode array may be expandable in order to improve the contact of one or more electrodes with a targeted cardiac tissue site. Expanding the tip array advantageously increases the spacing between electrodes to improve sensing and stimulation performance. Moreover, expansion of the tip array against the walls of a blood vessel stabilizes the lead position. If used as an endovascular lead, blood will easily flow between the expanded electrodes. A tip array may be expanded by advancing an expansion member toward the distal lead end. The expansion member is preferably conical such that as it is advanced through an electrode head assembly carrying the tip array, the widening circumference of the expansion member causes radial expansion of the electrodes in the array.

In one embodiment the expansion member may be a fixation helix mounted on a drive shaft that is coupled to a rotatable coil extending to the proximal lead end. Rotation of the proximal end of the coil causes rotation of the drive shaft, advancing the cone-shaped helix. The helix may be used as an active fixation device to further stabilize lead position. Alternatively, a conically-shaped expansion member may be mounted on a drive shaft having a screw-like head. A stylet equipped with a screwdriver-like blade may be used to engage the shaft head and, when rotated, cause advancement of the expansion member.

The lead provided by the present invention may be used with a cardiac pacing device or ICD equipped with a microprocessor-based control system for controlling device functions, a pulse generator for generating electrical impulses to be applied to the heart, and sense amplifiers for sensing cardiac signals. The device is preferably equipped with a switch matrix for selectively connecting one or more of the electrodes within an array in varying combinations for associated sensing and pacing functions. For example, one electrode within an array may be used for pacing and the other two electrodes within an array may be used for sensing the evoked response. Such a configuration advantageously overcomes the problem of polarization artifacts normally encountered when sensing for an evoked response using the same pair of electrodes as used for pacing. The pacing device or ICD is also equipped with a memory for storing cardiac data and, in particular, data relating to the pacing threshold or sensing threshold associated with various electrodes within an array.

In operation, the cardiac pacing device or ICD performs an electrode scan to determine which electrode or combination of electrodes within an array provides the lowest pacing threshold. Once the electrode configuration providing the lowest pacing threshold is identified, the control system of the device automatically selects this configuration as the pacing electrode configuration via the switch matrix. Alternatively or additionally, if an electrode array is to be used for sensing, a sensing threshold search may be performed in which the electrode(s) providing the highest signal amplitude or greatest signal-to-noise ratio may be determined and selected as the sensing electrode configuration via the switch matrix.

According to the present invention, when the lead is placed endovascularly for left heart applications, the electrode(s) within an array that are in closest contact with the heart tissue may be selected for stimulation and/or sensing. Stray current is minimized. If phrenic nerve stimulation or undesired atrial pacing occurs after implantation of a coronary sinus lead for left ventricular pacing, an alternative electrode within a given electrode array may be selected that still provides an acceptable pacing threshold at the targeted ventricular tissue site without extraneous stimulation.

According to the present invention, an electrode pair is selected for sensing an evoked response that is in the same vicinity of the paced tissue site but does not include the pacing electrode. In addition, battery longevity of the stimulation device may be improved by minimizing the surface area used to stimulate a targeted tissue site. A smaller electrode surface area associated with selecting one or two electrodes within an array increases the pacing impedance resulting in less current drawn from the battery. Furthermore, the electrode selection is "fine-tuned" by selecting only the electrode(s) within an array that provide the lowest pacing threshold, eliminating stray current and further extending the useful life of the device. Device performance may be also be improved by the ability to select an optimal sensing electrode configuration such that accurate sensing of cardiac signals is achieved.

The lead provided by the present invention may be stabilized by an expandable tip array and still be readily deployed and repositioned when used as an endovascular lead. Stabilizing the lead position over time may ensure stable pacing and/or sensing thresholds. By providing a lead with a reversible fixation device, the lead is easily advanced or retracted through a vascular pathway so that the surgical time required for positioning the lead may be reduced, with fewer complications encountered. If an electrode should fail, other electrodes within the same array may be used for targeting the same tissue site.

Thus a medical lead that allows accurate targeting of excitable tissue has been described and with which extraneous stimulation may be avoided and improved evoked response sensing may be achieved. The lead is readily deployed, secured and repositioned, if necessary, and provides alternative electrode configurations should a lead failure occur. A method for using the medical lead has also been described in which optimal electrode configurations may be automatically, or semi-automatically, selected. While the medical lead and associated method included in the present invention have been described according to specific embodiments in the above disclosure, these embodiments should be considered exemplary, rather than limiting, with regard to the following claims.

We claim:

1. An implantable medical device sensing cardiac depolarizations and delivering cardiac stimulation pulses, comprising:
    an implantable electrical lead having a plurality of electrodes located along a distal end;
    a pacer timing and control circuit coupled to the electrical lead; and a microprocessor coupled to the pacer timing and control circuit and executing a routine comprising a set of instructions to perform a threshold search to determine a combination of lead electrodes that provides an optimal threshold for sensing cardiac depolarizations and delivering cardiac stimulation pulses, wherein the microprocessor routine includes making a sensing threshold search comprising a sensing threshold measurement.

2. The implantable medical device of claim 1, wherein the microprocessor routine further includes determining a signal-to-noise ratio.

3. An implantable medical device sensing cardiac depolarizations and delivering cardiac stimulation pulses, comprising:
    an implantable electrical lead having a plurality of electrodes located along a distal end;
    a pacer timing and control circuit coupled to the electrical lead; and a microprocessor coupled to the pacer timing and control circuit and executing a routine comprising a set of instructions to perform a threshold search to determine a combination of lead electrodes that provides an optimal threshold for sensing cardiac depolarizations and delivering cardiac stimulation pulses, wherein the microprocessor routine includes making a pacing threshold search comprising a pacing threshold measurement.

4. An implantable medical device sensing cardiac depolarizations and delivering cardiac stimulation pulses, comprising:
    an implantable electrical lead having a plurality of electrodes located along a distal end;
    a pacer timing and control circuit coupled to the electrical lead; and a microprocessor coupled to the pacer timing and control circuit and executing a routine comprising a set of instructions to perform a threshold search to determine a combination of lead electrodes that provides an optimal threshold for sensing cardiac depolarizations and delivering cardiac stimulation pulses, wherein the plurality of electrodes are arranged in a staggered relative position.

5. An implantable medical device sensing cardiac depolarizations and delivering cardiac stimulation pulses, comprising:
    an implantable electrical lead having a plurality of electrodes located along a distal end;
    a pacer timing and control circuit coupled to the electrical lead; and a microprocessor coupled to the pacer timing and control circuit and executing a routine comprising a set of instructions to perform a threshold search to determine a combination of lead electrodes that provides an optimal threshold for sensing cardiac depolarizations and delivering cardiac stimulation pulses, wherein the microprocessor routine includes making an electrode scan that is enabled and disabled by a telemetry signal.

6. An implantable medical device sensing cardiac depolarizations and delivering cardiac stimulation pulses, comprising:
    an implantable electrical lead having a plurality of electrodes located along a distal end;
    a pacer timing and control circuit coupled to the electrical lead; and a microprocessor coupled to the pacer timing and control circuit and executing a routine comprising a set of instructions to perform a threshold search to determine a combination of lead electrodes that provides an optimal threshold for sensing cardiac depolarizations and delivering cardiac stimulation pulses, wherein the microprocessor routine includes selecting electrodes to be used for sensing cardiac depolarizations and for delivering cardiac pacing pulses, and wherein selecting the electrodes for the optimal sensing and pacing threshold is performed automatically.

7. An implantable medical device sensing cardiac depolarizations and delivering cardiac stimulation pulses, comprising:
    an implantable electrical lead having a plurality of electrodes located along a distal end;
    a pacer timing and control circuit coupled to the electrical lead; and a microprocessor coupled to the pacer timing and control circuit and executing a routine comprising a set of instructions to perform a threshold search to determine a combination of lead electrodes that provides an optimal threshold for sensing cardiac depolarizations and delivering cardiac stimulation pulses, wherein the lead further comprises an expansion member expanding the plurality of electrodes to vary an inter-electrode distance.

8. An implantable medical device sensing cardiac depolarizations and delivering cardiac stimulation pulses, comprising:
    an implantable electrical lead having a plurality of electrodes located along a distal end;

a pacer timing and control circuit coupled to the electrical lead; and a microprocessor coupled to the pacer timing and control circuit and executing a routine comprising a set of instructions to perform a threshold search to determine a combination of lead electrodes that provides an optimal threshold for sensing cardiac depolarizations and delivering cardiac stimulation pulses, wherein the microprocessor routine comprises a set of instructions to automatically determine a combination of the electrodes that provides an optimal stimulation configuration and a combination of the electrodes that provides an optimal sensing configuration by performing an electrode scan wherein the pacing and sensing thresholds of electrode combinations are measured.

9. The implantable medical device of claim 8, wherein the optimal sensing configuration is identified as the electrode combination having the highest signal amplitude.

10. The implantable medical device of claim 8, wherein the optimal sensing configuration is identified as the electrode combination having the highest signal-to-noise ratio.

11. The implantable medical device of claim 8, wherein the optimal stimulation configuration is identified as the electrode combination having the lowest pacing threshold that captures targeted tissue without depolarizing non-targeted tissue.

12. An implantable medical device sensing cardiac depolarizations and delivering cardiac stimulation pulses, comprising:

an implantable electrical lead having a plurality of electrodes located along a distal end;

a pacer timing and control circuit coupled to the electrical lead; and a microprocessor coupled to the pacer timing and control circuit and executing a routine comprising a set of instructions to perform a threshold search to determine a combination of lead electrodes that provides an optimal threshold for sensing cardiac depolarizations and delivering cardiac stimulation pulses, wherein the microprocessor routine adopts a default electrode configuration for pacing and sensing until a more optimal configuration is identified.

* * * * *